United States Patent [19]
Turner

[11] 3,981,030
[45] Sept. 21, 1976

[54] SUNBATHING ACCESSORY

[76] Inventor: Jeanette A. Turner, P.O. Box 7204, Greensboro, N.C. 27407

[22] Filed: May 27, 1975

[21] Appl. No.: 581,108

[52] U.S. Cl. ................................. 5/327 R; 211/43; 297/439
[51] Int. Cl.² .......................................... A47C 21/00
[58] Field of Search ...................... 5/327 R; 108/61; 211/42, 43; 269/328; 297/439

[56] References Cited
UNITED STATES PATENTS

| | | | |
|---|---|---|---|
| 2,170,724 | 8/1939 | Marquardt | 297/439 X |
| 2,478,497 | 8/1949 | Morrison | 5/327 R |
| 3,234,623 | 2/1966 | Rector | 5/327 R X |
| 3,425,565 | 2/1969 | Sprenger | 211/43 |

*Primary Examiner*—James C. Mitchell

[57] ABSTRACT

A base having a pair of spaced apart, upstanding end members, which are so configured and spaced apart as to maintain the feet of the sunbather in an erect position thereby insuring proper orientation of the legs to provide an even tan.

4 Claims, 3 Drawing Figures

SUNBATHING ACCESSORY

BACKGROUND OF THE INVENTION

Many people enjoy sunbathing, either for the general relaxation of the body provided by the warmth of the sun or for the pleasure derived from obtaining an even tan of the skin. For such people sunbathing is a practice requiring numerous aids to ensure obtaining maximum benefit from the time spent in the sun. Many such aids have been manufactured including such devices as reflectors to direct the sun rays to the body, special shields to protect certain areas of the body, headrests, mattresses, etc. However, to this inventor's knowledge, there is no device available for supporting and maintaining the feet and legs in the proper orientation for obtaining an even tan of the legs when the body is in a reclining position.

The problem arises from the natural tendency when the body is in a reclined, relaxed position, for the feet and legs will normally turn outward. This outward turning prevents even tanning of the skin on the outer side areas of the legs and feet, and additionally, this normal body position is generally uncomfortable.

SUMMARY OF THE INVENTION

The present invention is directed to a foot support for use in sunbathing and is of a shape permitting the feet to be comfortably held in an upright or erect position between opposing retaining walls of the support.

A preferred embodiment of the invention is molded in one piece from a hard plastic material, the size and weight permitting it to be easily carried in a beach bag or in the hand. There are no parts to be assembled prior to use. The opposed retaining walls are so spaced and configured as to engage the outer foot edges, preventing the normal tendency of the feet to turn outwardly. It is only necessary to place the heels in the concave areas of the base between the foot retaining walls. The feet are thus held in an upright position, thereby preventing the undesirable outward turning of the legs.

A second embodiment includes hinged, adjustable retaining walls, so that the device can be adjusted for comfortable use by various people.

It is therefore an object of the invention to provide a sunbathing device which maintains the feet erect when the body is in a reclined, relaxed position.

It is a further object of the invention to provide a device of the type described for use during sunbathing that is lightweight and of a size that may be easily carried by the user.

Still further objects and uses of the invention will become apparent after a study of the following detailed description in conjunction with the accompanying drawings, in which.

DETAILED DESCRIPTION OF THE INVENTION

Figure 1:
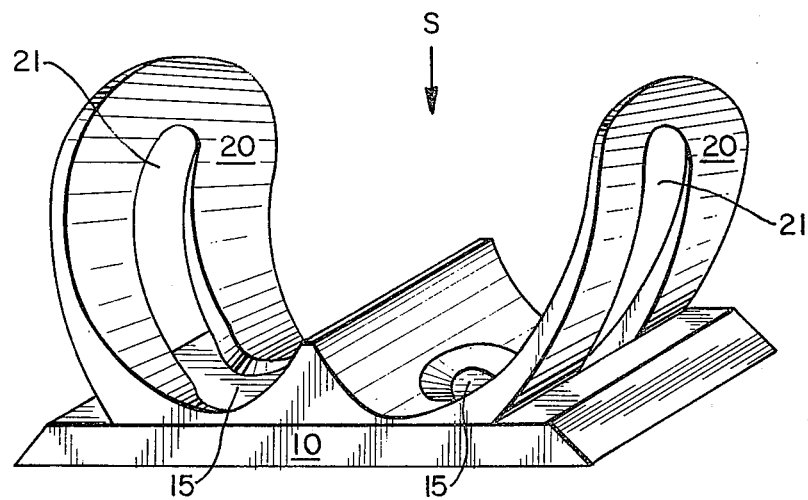
FIG. 1 is a perspective view of a sunbathing device made in accordance with the present invention.

Turning now to a discussion of the accompanying drawings, in FIG. 1 the foot support S according to the present invention is of an integrally formed construction, molded from any of the stronger, more rigid plastics such as the high density plastic materials. Although other materials may be used, plastic is more suitable because metal is too heat conductive and could burn the feet, and glass is generally not acceptable in sunbathing areas such as pools and beaches.

In this preferred embodiment, the support S has no moving parts and comprises a base means 10 having recessed areas 15 therein for comfortably receiving the heels of a reclined sunbather. A pair of feet retaining end walls 20 extend upwardly from opposite ends of base 10 for holding the feet erect. The shape of end walls 20 and the distance therebetween are so selected as to maintain comfortable pressure against the outside of the feet when erect, and not allow the feet to turn outwardly. Although the end wall configuration and shape is not critical, in the illustrated embodiment, the space between the end walls is approximately 7 – 7½ inches, which is approximately the combined widths of the feet of a sunbather of normal size. The front-to-rear depth of base 10 and side walls 20 in the preferred embodiment is approximately 3 inches, however it is only necessary that the overall depth of S must be enough to provide comfortable support for the sides and heels of the feet.

The molded shape of support S includes base 10 which preferably has a flat, ground or pool deck engaging undersurface. The upper surface of base 10 has the aforementioned recessed areas 15 which receive the heels of the user. These recessions 15 are not absolutely essential to the invention, and the base 10 may have a flat upper surface, but they do provide support and often some retaining effect for the heels. Areas 15 may extend the full depth of base 10, as in FIG. 3, or may be an extension of an elongated opening 21 in the foot retaining wall as in FIG. 1.

End retaining members 20 extend immovably upward from each end of base 10 approximately 4–6 inches or about half way up the outer side of the foot of the sunbather.

Figure 2:
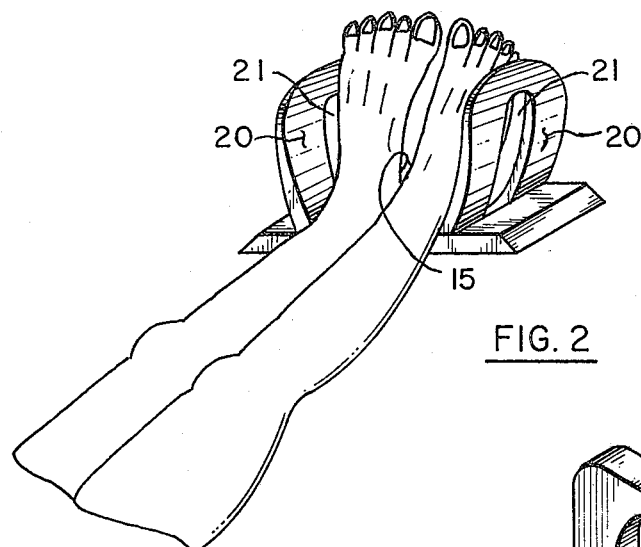
FIG. 2 is a perspective view of the devices of FIG. 1 illustrated in use.

In use, as illustrated in FIG. 2, the support S is placed on the ground surface at the feet of the user. When the individual reclines, the backs of the heels are placed in concave areas 15, and the feet are thereby supported upright by retaining members 20. The outer sides of the feet may rest within openings 21 which permit air circulation and access to the sun's rays.

Figure 3:
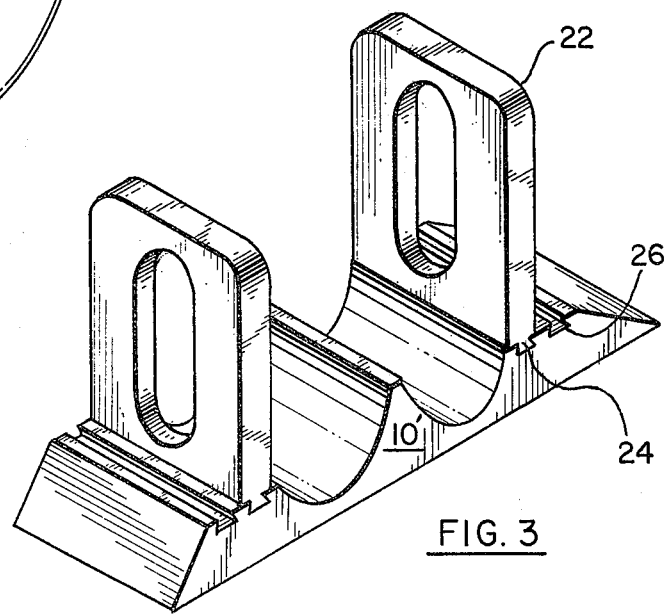
FIG. 3 is a perspective view of an alternate embodiment of the invention.

FIG. 3 illustrates an alternate embodiment of the present invention wherein a means is provided for varying the spacing between side retaining means 22. This provides some latitude for the purpose of meeting variances in personal preference or individual foot size.

In the alternate embodiment each side retaining means 22 is formed in essentially the same shape as side retaining means 20 in FIG. 1 except that the side retaining members 22 are removably attached to base 10' rather than integrally formed as in FIG. 1. In FIG. 3 each side retaining member 22 is removably joined to base 10 by means of dovetail joint which is formed when a protrusion or tenon 24 which extends along the length of the lower edge of side retainer 22 is slipped into a cooperatively shaped mortise 26 in the upper surface of the base 10'. A pair of mortises 26 are spaced slightly apart on each side of the base 10. Therefore, the distance between opposing side retaining members 22 may be adjusted to accommodate feet of different sizes.

Various other changes and modifications may be made to the embodiment described hereinabove without departing from the scope and intent of the invention which is limited only by the following claims.

What is claimed is:
1. A foot support for sunbathers comprising:
   a. a base member having an upper surface and a pair of foot retaining end walls extending upwardly from spaced points along the upper surface;
   b. said base member further including a pair of spaced depressions therein between said end walls for receiving the heels of a sunbather when in the reclined position;
   c. said end walls including a foot engaging portion adjacent the upper end and having a vertical dimension of such magnitude that, when occupied, the foot engaging portion engages only the outer edge of the sunbather's foot at a point more than half-way up from the heel toward the toes;
   d. said end walls being spaced apart a distance substantially equal to the combined width of the feet of a normally sized sunbather.

2. The sunbathing accessory according to claim 1 wherein said end members are removably supported by said base means, whereby said accessory can be disassembled to facilitate packing and storage.

3. The sunbathing accessory according to claim 1 and further including adjusting means associated with said end members for varying the spacing between said end members.

4. The sunbathing accessory according to claim 3 wherein said foot retaining end members each include a projection means depending therefrom, said base means include a plurality of grooves located at prescribed intervals therein, said projection means inserted into selected grooves to vary the spacing of said end members.

* * * * *